US011602277B2

(12) United States Patent
Chiba

(10) Patent No.: US 11,602,277 B2
(45) Date of Patent: Mar. 14, 2023

(54) ENDOSCOPE SYSTEM AND IMAGE DISPLAY DEVICE

(71) Applicant: HOYA CORPORATION, Tokyo (JP)

(72) Inventor: Toru Chiba, Tokyo (JP)

(73) Assignee: HOYA CORPORATION, Tokyo (JP)

(*) Notice: Subject to any disclaimer, the term of this patent is extended or adjusted under 35 U.S.C. 154(b) by 945 days.

(21) Appl. No.: 16/468,956

(22) PCT Filed: Jan. 11, 2018

(86) PCT No.: PCT/JP2018/000423
§ 371 (c)(1),
(2) Date: Jun. 12, 2019

(87) PCT Pub. No.: WO2018/131631
PCT Pub. Date: Jul. 19, 2018

(65) Prior Publication Data
US 2019/0335978 A1    Nov. 7, 2019

(30) Foreign Application Priority Data
Jan. 16, 2017  (JP) .............................. JP2017-005446

(51) Int. Cl.
*A61B 1/00*   (2006.01)
*A61B 1/045*  (2006.01)
(Continued)

(52) U.S. Cl.
CPC ........ *A61B 5/0075* (2013.01); *A61B 1/00045* (2013.01); *A61B 1/000094* (2022.02);
(Continued)

(58) Field of Classification Search
None
See application file for complete search history.

(56) References Cited

U.S. PATENT DOCUMENTS

| 2007/0041640 | A1* | 2/2007 | Tabata | .................... G06T 5/008 |
| | | | | 382/173 |
| 2016/0058274 | A1 | 3/2016 | Chiba | |
| 2016/0146723 | A1* | 5/2016 | Chiba | ................ G01N 33/4833 |
| | | | | 250/208.1 |

FOREIGN PATENT DOCUMENTS

| JP | 2004-303193 A | 10/2004 |
| JP | 2006-326153 A | 12/2006 |

(Continued)

OTHER PUBLICATIONS

U.S. Appl. No. 16/468,972 to Toru Chiba, filed Jun. 12, 2019.
International Search Report issued in WIPO Patent Application No. PCT/JP2018/000423, dated Mar. 20, 2018.

*Primary Examiner* — John P Leubecker
*Assistant Examiner* — Minqiao Huang
(74) *Attorney, Agent, or Firm* — Greenblum & Bernstein, P.L.C.

(57) ABSTRACT

An endoscope system includes: a processor that generates first and second feature amount distribution images of a living tissue from an imaged image of the living tissue and generates a second feature amount distribution processed image from these distribution images; and a display that displays the second feature amount distribution processed image. The processor generates a mask image of the second feature amount distribution image by, in the first feature amount distribution image, setting a pixel whose pixel value representing the first feature amount is less than a lower limit value as a non-transmissive pixel having a transmittance of zero and setting a pixel between an upper limit value and the lower limit value as a transmissive pixel while giving the pixel a transmittance determined continuously or stepwise in accordance with the pixel value in the first feature amount distribution image.

7 Claims, 10 Drawing Sheets

(51) Int. Cl.
*A61B 5/00* (2006.01)
*A61B 1/06* (2006.01)
*A61B 5/1455* (2006.01)
*G02B 23/24* (2006.01)
*G02B 23/26* (2006.01)

(52) U.S. Cl.
CPC .......... *A61B 1/00186* (2013.01); *A61B 1/045* (2013.01); *A61B 1/0676* (2013.01); *A61B 5/1455* (2013.01); *G02B 23/2407* (2013.01); *G02B 23/26* (2013.01)

(56) References Cited

FOREIGN PATENT DOCUMENTS

| | | | |
|---|---|---|---|
| JP | 2013-118978 | A | 6/2013 |
| JP | 2013118978 | a * | 6/2013 |
| JP | 2014-230647 | A | 12/2014 |
| JP | 2014-233344 | A | 12/2014 |
| JP | 2014233344 | a * | 12/2014 |
| JP | 2015-198735 | A | 11/2015 |
| JP | 2015198735 | a * | 11/2015 |
| JP | 2016-52391 | A | 4/2016 |
| JP | 2016-097067 | A | 5/2016 |
| JP | 2016-220802 | A | 12/2016 |
| WO | 2006/129740 | A1 | 12/2006 |
| WO | 2013/084719 | A1 | 6/2013 |

* cited by examiner

ENDOSCOPE SYSTEM AND IMAGE DISPLAY DEVICE

TECHNICAL FIELD

The present disclosure relates to an endoscope system and an image display device that perform display of an image by processing a feature amount of a living tissue into the image.

BACKGROUND ART

There is an endoscope system having a function of obtaining information on a biological substance in a living tissue, which is a subject, for example, a hemoglobin concentration or a hemoglobin oxygen saturation, from image data obtained by an endoscope and displaying a distribution image representing the information as a distribution. With such a distribution image of a feature amount, it is possible to provide a lesion or a part suspected as the lesion (hereinafter, the lesion or the part suspected as the lesion will be referred to as a non-healthy part) as powerful diagnosis support information. Patent Literature 1 describes an example of a hemoglobin observation apparatus including such an endoscope system.

The hemoglobin observation apparatus described in Patent Literature 1 has a configuration in which information of reflected light of three different wavelength bands of hemoglobin contained in an object to be observed is processed based on a predetermined arithmetic processing, and the processing result is displayed on a display unit. At this time, a hemoglobin oxygen saturation is calculated based on a correlation between information on the amount of reflected or transmitted light depending on a hemoglobin concentration and information on the amount of reflected or transmitted light depending on oxygen saturation, in the arithmetic processing of a signal of a captured image.

CITATION LIST

Patent Literature

Patent Literature 1: JP 2006-326153 A
Summary of Disclosure
Technical Problem

SUMMARY OF INVENTION

Technical Problem

An image representing a distribution of the oxygen saturation calculated and displayed by the above-described hemoglobin observation apparatus including the endoscope system is lack of information to identify a location in visceral tissues and blood vessels such as veins and arteries. Thus, a positional relationship between a part of interest and a living tissue is unclear, which is not appropriate as a diagnosis support image. That is, it is difficult to clearly identify which position of the living tissue corresponds to the part of interest in the image representing the oxygen saturation distribution. In addition, even when the image of the living tissue is arranged on a screen so as to be observed simultaneously with the oxygen saturation image, it is difficult to grasp any position of the living tissue where the oxygen saturation is high, that is, a positional relationship between the living tissue and the oxygen saturation, which is disadvantageous.

Therefore, an object of the present disclosure is to provide an endoscope system and an image display device that display clear image information with which it is possible to detect presence of a non-healthy part including a lesion or a part suspected as the lesion in a living tissue based on an oxygen saturation and a hemoglobin concentration and it is possible to identify any position in the living tissue where the non-healthy part of interest as a diagnosis support image is present.

Solution to Problem

One aspect of the present disclosure is an endoscope system.

An endoscope system includes: an endoscope including an imaging element configured to generate a plurality of pieces of image data by imaging a living tissue; a processor including a first image processing unit configured to obtain a first feature amount distribution image representing a distribution of a first feature amount of the living tissue and a second feature amount distribution image representing a distribution of a second feature amount of the living tissue from the plurality of pieces of image data, a second image processing unit configured to generate a mask image to mask the second feature amount distribution image from the first feature amount distribution image by, in the first feature amount distribution image, setting a pixel having the first feature amount less than a predetermined threshold as a non-transmissive pixel having a transmittance of zero and setting a pixel having the first feature amount equal to or more than the predetermined threshold as a transmissive pixel while giving the pixel a transmittance, determined in accordance with a degree of the first feature amount deviating from the threshold, and a third image processing unit configured to generate a second feature amount distribution processed image in which the mask image is superimposed on an upper layer of the second feature amount distribution image; and a display configured to display the second feature amount distribution processed image generated by the third image processing unit.

For example, it is preferable that the second image processing unit generate a mask from the first feature amount distribution image and generate a mask image for filtering of the second feature amount distribution image by setting a pixel having the first feature amount less than a predetermined lower limit value as a non-transmissive pixel having a transmittance of zero, setting a pixel having the first feature amount equal to or more than a predetermined upper limit value as a transmissive pixel having a transmittance of 100%, and setting the pixel whose output value is between the lower limit value and the upper limit value as the transmissive pixel while giving the pixel a transmittance to be modulated in accordance with a distance from the lower limit value to the output value.

It is preferable that the transmittance of the transmissive pixel increase continuously or stepwise as the first feature amount of the pixel deviates more from the threshold. For example, the transmittance of the transmissive pixel can be configured to increase continuously or stepwise from the lower limit value to the upper limit value.

It is preferable that the transmittance of the transmissive pixel increase nonlinearly as the first feature amount of the pixel deviates more from the threshold. For example, the transmittance of the transmissive pixel can be configured to increase nonlinearly in accordance with the degree of the first feature amount of the pixel deviating from the threshold, or as the output value of the pixel changes from the lower limit value to the upper limit value.

It is preferable that the processor include an input unit configured to receive an input that continuously changes a value of the threshold, and that the third image processing unit be configured to generate the second feature amount distribution processed image each time the input is changed.

The first image processing unit preferably calculates values of a first ratio and a second ratio between predetermined components using values of the components out of components of the plurality of pieces of image data and calculates the first feature amount and the second feature amount using the values of the first ratio and the second ratio. The first feature amount is preferably a hemoglobin concentration, and the second feature amount is preferably a hemoglobin oxygen saturation.

It is preferable that the first ratio be a ratio sensitive to the first feature amount of the living tissue, that the second ratio be a ratio sensitive to the second feature amount of the living tissue, that one of the components of the image data used for calculation of the first ratio be a component of a first wavelength band within a range of 500 nm to 600 nm, and that one of the components of the image data used for calculation of the second ratio be a component of a second wavelength band narrower than the first wavelength band.

Another aspect of the disclosure is an image display device comprising a processor configured to perform image processing and a display configured to display an image.

The image display device includes: the processor that includes: a first image processing unit configured to obtain a first feature amount distribution image representing a distribution of a first feature amount of a living tissue and a second feature amount distribution image representing a distribution of a second feature amount of the living tissue from an imaged image of the living tissue; a second image processing unit configured to generate a mask image to mask the second feature amount distribution image from the first feature amount distribution image by, in the first feature amount distribution image, setting a pixel having the first feature amount less than a predetermined threshold as a non-transmissive pixel having a transmittance of zero and setting a pixel having the first feature amount equal to or more than the predetermined threshold as a transmissive pixel while giving the pixel a transmittance, determined in accordance with a degree of a pixel value of the pixel deviating from the threshold; and a third image processing unit configured to generate a second feature amount distribution processed image in which the mask image is superimposed on an upper layer of the second feature amount distribution image; and the display that displays the second feature amount distribution processed image generated by the third image processing unit.

For example, it is preferable that the second image processing unit generate a mask from the first feature amount distribution image and generate a mask image for filtering of the second feature amount distribution image by setting a pixel having the first feature amount less than a predetermined lower limit value as a non-transmissive pixel having a transmittance of zero, setting a pixel having the first feature amount equal to or more than a predetermined upper limit value as a complete-transmissive pixel having a transmittance of one, and setting the pixel whose output value is between the lower limit value and the upper limit value as the transmissive pixel while giving the pixel a transmittance to be modulated in accordance with a distance from the lower limit value to the output value.

Advantageous Effects

According to the endoscope system and the image display device described above, it is possible to display the image including clear image information with which it is possible to identify any position in the living tissue where the non-healthy part of interest is present as the diagnosis support image, the diagnosis support image with which it is possible to detect the presence of the non-healthy part including the lesion or the part suspected as the lesion in the living tissue.

DESCRIPTION OF EMBODIMENTS

Figure 1A:
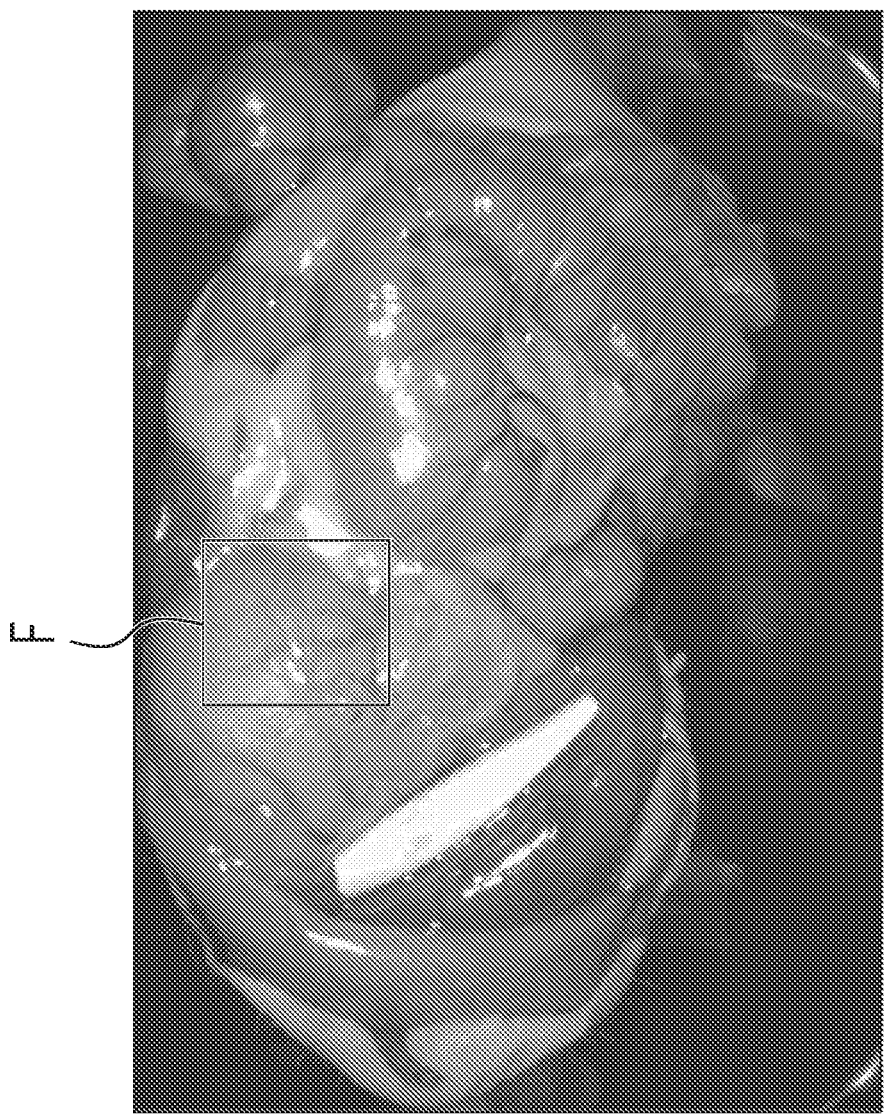
FIGS. 1(a) to 1(c) are views illustrating examples an image of a living tissue and a distribution image of a biological feature amount of the living tissue.
Figure 1B:
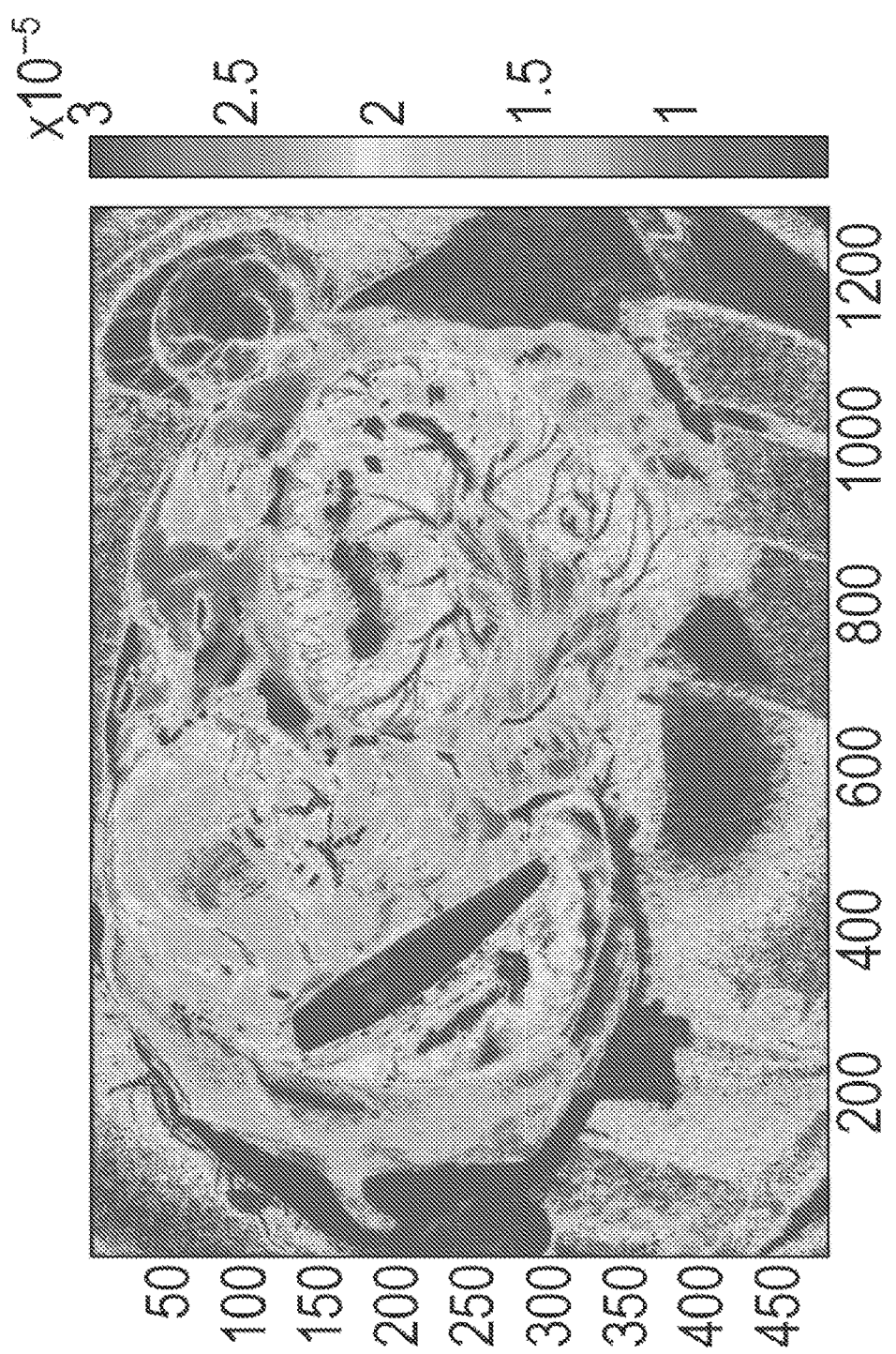
Figure 1C:
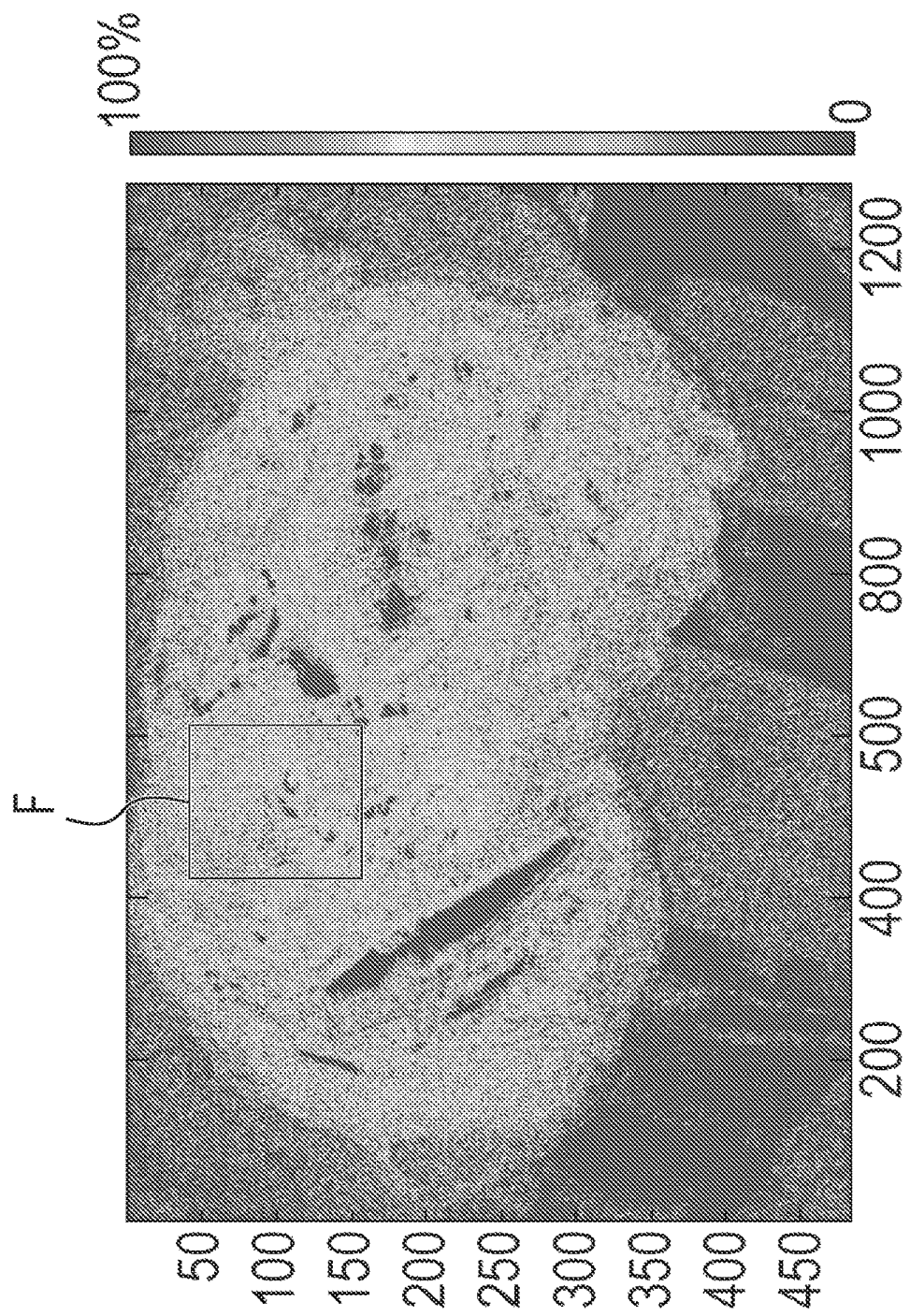

An endoscope system or an image display device according to an embodiment of the present disclosure displays a diagnosis support image capable of determining presence or absence of a non-healthy part in a living tissue. FIGS. 1(a) to 1(c) are views illustrating examples an image of the living tissue and a distribution image of a biological feature amount of the living tissue.

FIG. 1(a) illustrates an example of an image of the living tissue. FIG. 1(b) illustrates an example of a distribution image of a hemoglobin concentration (biological feature amount) in the living tissue calculated using the endoscope system to be described later, and FIG. 1(c) illustrates an example of a distribution image of an oxygen saturation (biological feature amount) in the living tissue calculated using the endoscope system to be described later.

In FIG. 1(b), a muscle-like form such as a blood vessel of the living tissue is illustrated. On the other hand, the form of the blood vessel of the living tissue is not clearly illustrated in the distribution image of the oxygen saturation illustrated in FIG. 1(c). Thus, it is necessary to find a part with a low oxygen saturation from an oxygen saturation distribution image and determine a level of a hemoglobin concentration corresponding to the part in order to detect a tissue having a high hemoglobin concentration and a low oxygen saturation which are characterized as a malignant tumor or the like. However, it is difficult to instantaneously identify which part of the living tissue illustrated in FIG. 1(a) corresponds to a lesion or a non-healthy part suspected as the lesion from the oxygen saturation distribution image, that does not include image information that can identify a location of a blood vessel or the like of the living tissue even if FIG. 1(b) and FIG. 1(c) are displayed in parallel on a display.

In the embodiment of the present disclosure, it is possible to provide the diagnosis support image with which it is possible to detect presence of such a non-healthy part including the lesion or the part suspected as the lesion in the living tissue and to easily identify a position of the non-healthy part in the living tissue. That is, an image added with information reflecting a shape and a position of the living tissue is provided as the diagnosis support image.

(Diagnosis Support Image)

Figure 2A:
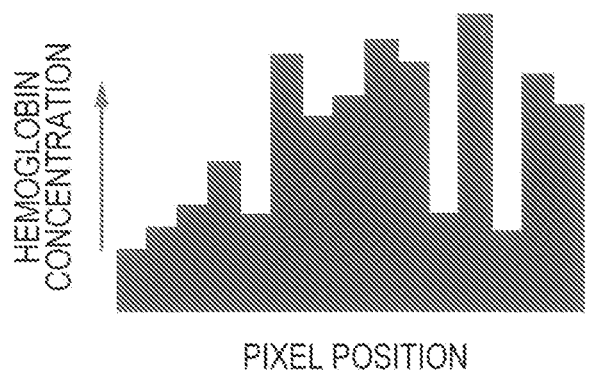
FIGS. 2(a) to 2(c) are views for describing an example of creation of a diagnosis support image to be displayed by an endoscope system or an image display device of the present embodiment.
Figure 2B:
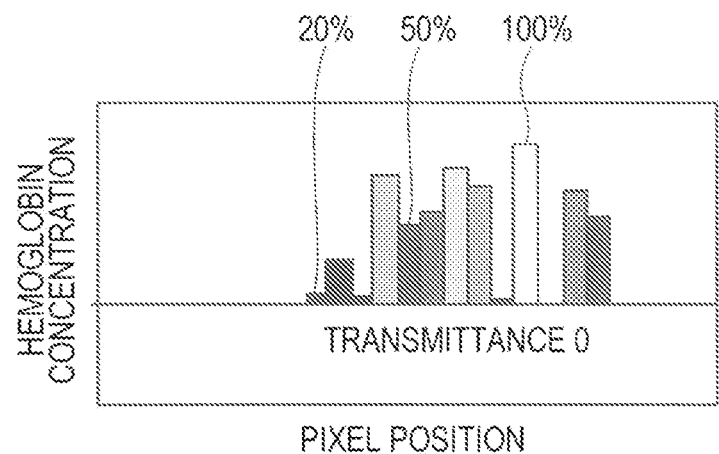
Figure 2C:
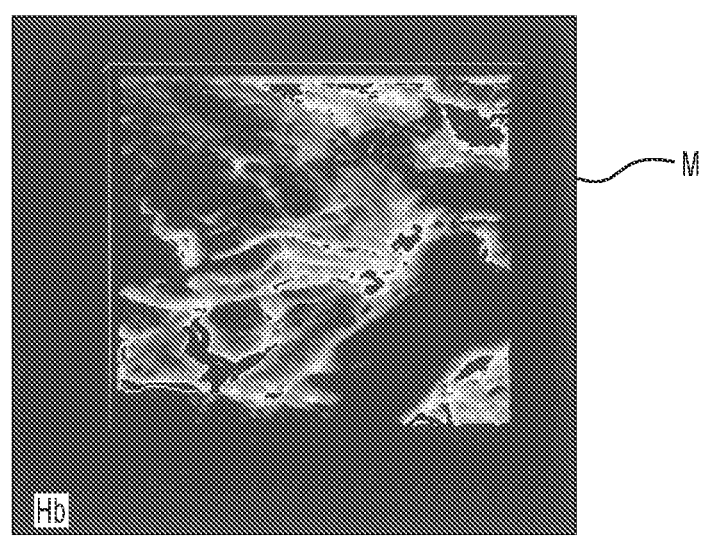

FIGS. 2(a) to 2(c) are views for describing an example of creation of the diagnosis support image to be displayed by the endoscope system or the image display device of the present embodiment.

In the present embodiment, a mask image to mask a distribution image of an oxygen saturation (second feature amount) illustrated in FIG. 1(c) is generated from a distribution image of a hemoglobin concentration (first feature amount) illustrated in FIG. 1(b). Specifically, in the present embodiment, a pixel having the hemoglobin concentration (first feature amount) at each pixel less than a predetermined threshold is set as a non-transmissive pixel having a transmittance of zero, and a pixel having the hemoglobin concentration equal to or more than the threshold is set as a transmissive pixel while giving the pixel a transmittance, determined in accordance with a degree of the hemoglobin concentration deviating from the threshold, as illustrated in FIG. 2(b) in a distribution of the hemoglobin concentration calculated by the endoscope system to be described later (see FIG. 2(a)). Specifically, the mask image is created from a distribution image of the hemoglobin concentration (first feature amount) by setting a pixel having an output value of each pixel, that is, a pixel value relating to the hemoglobin concentration equal to or more than a predetermined lower limit value (a pixel value corresponding to the threshold of the hemoglobin concentration) as the transmissive pixel while giving the pixel a transmittance determined in accordance with a difference (distance) between the pixel value and the lower limit value such that the transmittance becomes higher from the lower limit value to an upper limit value.

The endoscope system and the image display device according to the present embodiment create this mask image as the mask image to mask the oxygen saturation distribution image, creates an oxygen saturation processed distribution image in which the mask image is superimposed on an upper layer of the oxygen saturation distribution image as a diagnosis support image, and display an oxygen saturation distribution processed image on the display.

In the example illustrated in FIG. 2(a), 20%, 50% and 100% of transmittances are illustrated. When the transmittance is used as the mask image, a luminance value of a pixel of an image in a lower layer of the mask image is changed in accordance with to the transmittance. At each pixel of the mask image, the transmittance of 100% means no change of the luminance value of the pixel of the image in the lower layer of the mask image, and the transmittance of 25% means a change of the luminance value of the pixel of the image in the lower layer of the mask image to 25%.

FIG. 2(c) illustrates an example of a mask image M.

(Configuration of Endoscope System)

Figure 3:
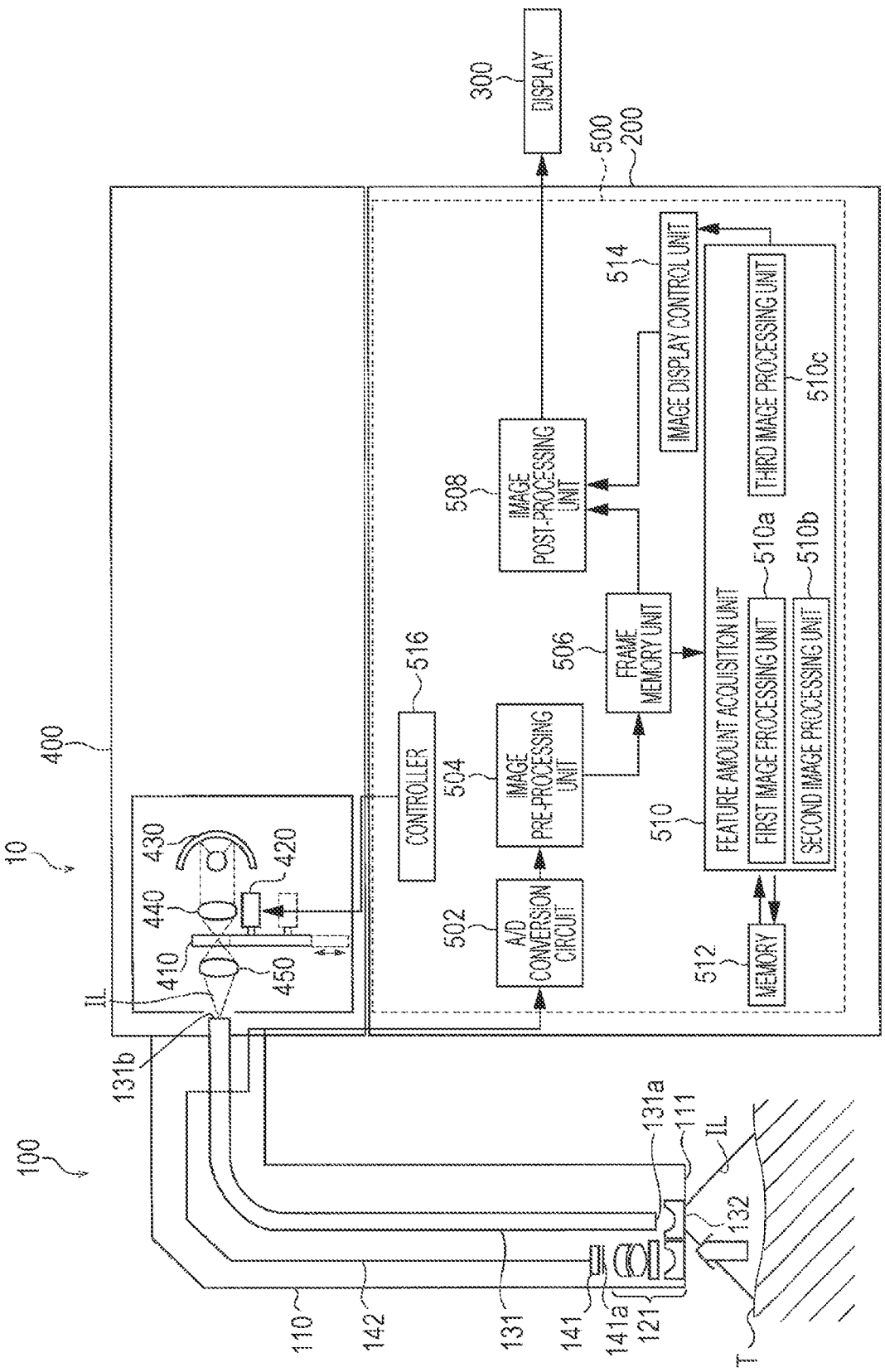
FIG. 3 is a block diagram of a configuration of an example of the endoscope system used in the present embodiment.

FIG. 3 is a block diagram illustrating a configuration of an endoscope system 10 of the present embodiment. The endoscope system 10 includes an electronic endoscope (endoscope) 100, a processor 200, a display 300, and a light source device 400. The electronic endoscope 100 and the display 300 are detachably connected to the processor 200. The processor 200 includes an image processing unit 500. The light source device 400 is detachably connected to the processor 200.

The electronic endoscope 100 has the insertion tube 110 to be inserted into a body of a subject. Inside the insertion tube 110, a light guide 131 extending substantially over the entire length of the insertion tube 110 is provided. A distal end 131a which is one end of the light guide 131 is positioned at the distal end of the insertion tube 110, that is, in the vicinity of an insertion tube distal end 111, and a proximal end 131b which is the other end of the light guide 131 is positioned at a connection portion with the light source device 400. Therefore, the light guide 131 extends from the connection portion with the light source device 400 to the vicinity of the insertion tube distal end 111.

The light source device 400 includes, as a light source, a light source lamp 430 that generates light having a large amount of light such as a xenon lamp. The light emitted from the light source device 400 is incident on the proximal end 131b of the light guide 131 as illumination light IL. The light incident on the proximal end 131b of the light guide 131 is guided to the distal end 131a through the light guide 131 and emitted from the distal end 131a. At the insertion tube distal end 111 of the electronic endoscope 100, a light distribution lens 132 disposed so as to oppose the distal end 131a of the light guide 131 is provided. The illumination light IL emitted from the distal end 131a of the light guide 131 passes through the light distribution lens 132 and illuminates a living tissue T in the vicinity of the insertion tube distal end 111.

At the insertion tube distal end 111 of the electronic endoscope 100, an objective lens group 121 and an imaging element 141 are provided. The objective lens group 121 and the imaging element 141 form an imaging unit. Light reflected or scattered on a surface of the living tissue T out of the illumination light IL is incident on the objective lens group 121 and is condensed to form an image on a light-receiving surface of the imaging element 141. As the imaging element 141, it is possible to use a known imaging element such as a charge coupled device (CCD) image sensor for imaging a color image provided with a color filter 141a on a light-receiving surface thereof and a complementary metal oxide semiconductor (CMOS) image sensor.

Figure 4:
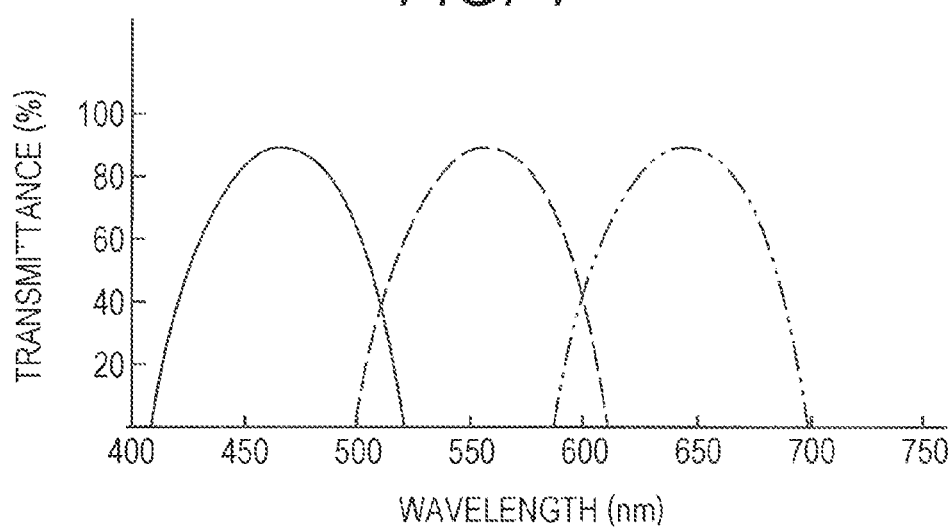
FIG. 4 is a graph illustrating an example of spectral characteristics of the respective filters of red (R), green (G) and blue (B) of an imaging element of the endoscope system used in the present embodiment.

The color filter 141a is a so-called on-chip filter which is formed directly on each light-receiving element of the imaging element 141 and in which an R color filter that passes red light, a G color filter that passes green light, and a B color filters that passes blue light are arrayed. FIG. 4 is a graph illustrating an example of spectral characteristics of the respective filters of red (R), green (G) and blue (B) of the imaging element used in the present embodiment. The R color filter of the present embodiment is a filter that passes light having a wavelength longer than a wavelength of about 570 nm (for example, 580 nm to 700 nm), the G color filter is, for example, a filter that passes light having a wavelength of about 470 nm to 620 nm, and the B color filter is a filter that passes light having a wavelength shorter than a wavelength of about 530 nm (for example, 420 nm to 520 nm).

The imaging element 141 is an imaging means that images the living tissue T illuminated by each of a plurality of beams of lights, and generates color image data corresponding to each of the beams of light, and is an image data generation means that illuminates the living tissue T with a plurality of beams of light having different wavelength ranges to generate color image data corresponding to the light reflected or scattered on the living tissue T. The imaging element 141 is controlled to be driven in synchronization with the image processing unit 500 to be described later, and outputs color image data corresponding to an image of the living tissue T imaged on the light-receiving surface periodically (for example, at intervals of 1/30 seconds). The color image data output from the imaging element 141 is sent to the image processing unit 500 of the processor 200 via a cable 142.

The image processing unit 500 mainly includes an A/D conversion circuit 502, an image pre-processing unit 504, a frame memory unit 506, and an image post-processing unit 508, a feature amount acquisition unit 510, a memory 512, an image display control unit 514, and a controller 516.

The A/D conversion circuit 502 A/D converts the color image data input from the imaging element 141 of the electronic endoscope 100 via the cable 142 and outputs digital data. The digital data output from the A/D conversion circuit 502 is sent to the image pre-processing unit 504.

The image pre-processing unit 504 generates color image data of R, G, and B components constituting an image by demosaicing digital data from R digital image data imaged by a light-receiving element in the imaging element 141 to which the R color filter is mounted, G digital image data imaged by a light-receiving element in the imaging element 141 to which the G color filter is mounted, and B digital image data imaged by a light-receiving element in the imaging element 141 to which the B color filter is mounted. In addition, the image pre-processing unit 504 is a part that performs predetermined signal processing such as color correction, a matrix operation, and white balance correction on the generated R, G, B color image data.

The frame memory unit 506 temporarily stores the color image data of each image which has been imaged by the imaging element 141 and subjected to the signal processing.

The image post-processing unit 508 reads the color image data stored in the frame memory unit 506 or receives image data generated by the image display control unit 514 to be described later and performs signal processing (γ correction or the like) on the received image data, thereby generating screen data to be displayed on the display. The image data generated by the image display control unit 514 includes data of a distribution image of a feature amount such as an oxygen saturation distribution image illustrating a distribution of a hemoglobin oxygen saturation of the living tissue T as will be described later. The generated screen data (video format signal) is output to the display 300. As a result, the image of the living tissue T, the distribution image of the feature amount of the living tissue T, and the like are displayed on a screen of the display 300.

In response to an instruction from the controller 516, the feature amount acquisition unit 510 calculates a hemoglobin concentration and the hemoglobin oxygen saturation of the imaged living tissue T as feature amounts and generates distribution images of these features on the image of the imaged living tissue T, that is, a distribution image indicating a distribution of the hemoglobin concentration and the oxygen saturation distribution image indicating the distribution of the hemoglobin oxygen saturation as will be described later. The feature amount acquisition unit 510 further generates the mask image to mask the oxygen saturation distribution image from the hemoglobin concentration distribution image. The feature amount acquisition unit 510 further generates the oxygen saturation distribution processed image in which the mask image is superimposed on the upper layer of the oxygen saturation distribution image.

Since the feature amount of the hemoglobin concentration or the hemoglobin oxygen saturation is calculated by an operation using the color image data of the living tissue T illuminated with the plurality of beams of light having different wavelength ranges, the feature amount acquisition unit 510 calls out the color image data and various types of information used in the feature amount acquisition unit 510 from the frame memory unit 506 or the memory 512.

The image display control unit 514 controls a form in which the generated oxygen saturation distribution processed image is displayed on the display 300.

The controller 516 is a part that performs not only an operation instruction and operation control of each part of the image processing unit 500 but also an operation instruction and operation control of each part of the electronic endoscope 100 including the light source device 400 and the imaging element 141.

Incidentally, the feature amount acquisition unit 510 and the image display control unit 514 may be configured by a software module that serves each of the above-described functions as a program is activated and executed on a computer, or may be configured by dedicated hardware.

In this manner, the processor 200 has both the function of processing the color image data output from the imaging element 141 of the electronic endoscope 100 and the function of instructing and controlling the operations of the electronic endoscope 100, the light source device 400, and the display 300.

The light source device 400 is a light-emitting means that emits first light, second light, and third light, and causes the first light, the second light, and the third light to be incident on the light guide 131. The light source device 400 of the present embodiment emits the first light, the second light, and the third light having different wavelength ranges, but may emit four or more beams of light. In this case, the fourth light may be light having the same wavelength range as that of the first light. The light source device 400 includes a condenser lens 440, a rotary filter 410, a filter control unit 420, and a condenser lens 450, in addition to the light source lamp 430. The light which is substantially parallel light and emitted from the light source lamp 430 is, for example, white light, is condensed by the condenser lens 440 and passes through the rotary filter 410, and then, is condensed again by the condenser lens 450, and is incident on the proximal end 131b of the light guide 131. Incidentally, the rotary filter 410 is movable between a position on an optical path of light radiated from the light source lamp 430 and a retreat position outside the optical path by a moving mechanism (not illustrated) such as a linear guideway. Since the rotary filter 410 includes a plurality of filters having different transmission characteristics, a wavelength range of light emitted from the light source device 400 differs depending on a type of the rotary filter 410 crossing the optical path of the light radiated from the light source lamp 430.

Incidentally, the configuration of the light source device 400 is not limited to that illustrated in FIG. 3. For example, a lamp that generates convergent light instead of the parallel light to the light source lamp 430 may be adopted. In this case, for example, a configuration in which light radiated from the light source lamp 430 is converged in front of the condenser lens 440 and is made incident on the condenser lens 440 as diffused light may be adopted. In addition, a configuration in which substantially parallel beams of light, generated by the light source lamp 430, are directly incident on the rotary filter 410 may be adopted instead of using the condenser lens 440. In addition, in the case of using the lamp that generates the convergent light, a configuration in which a collimator lens is used instead of the condenser lens 440 to cause light to be incident on the rotary filter 410 in the state of substantially parallel beams of light may be adopted. For example, when an interference-type optical filter, such as a dielectric multilayer film filter, is used as the rotary filter 410, it is possible to obtain more favorable filter characteristics by causing substantially parallel beams of light to be incident on the rotary filter 410 to make incident angles of the beams of light with respect to the optical filter uniform. In addition, a lamp that generates divergent light may be adopted as the light source lamp 430. Even in this case, it is possible to adopt the configuration in which the collimator lens is used instead of the condenser lens 440 to cause substantially parallel beams of light to be incident on the rotary filter 410.

In addition, the light source device 400 is configured to emit the plurality of beams of light having different wavelength ranges by transmitting the light radiated from the single light source lamp 430 to the optical filter, but it is also possible to use a semiconductor light source, such as a light-emitting diode and a laser element that outputs a laser beam, that emit a plurality of different beams of light having different wavelength bands, as a light source of the light source device 400, for example, instead of the light source lamp 430. In this case, the rotary filter 410 is not necessarily used. In addition, the light source device 400 can be also configured such that the light source device 400 separately emits, for example, combined white light including excitation light having a predetermined wavelength range and fluorescent light excited and emitted by the excitation light and light having a predetermined narrow wavelength range. The configuration of the light source device 400 is not particularly limited as long as the light source device 400 emits a plurality of beams of light having different wavelength ranges.

The rotary filter 410 is a disk-type optical unit having a plurality of optical filters, and is configured such that a passing wavelength range of light changes depending on a rotation angle thereof. The rotary filter 410 of the present embodiment includes three optical filters having different passing wavelength bands, but may have four, five, or six or more optical filters. The rotation angle of the rotary filter 410 is controlled by the filter control unit 420 connected to the controller 516. The controller 516 controls the rotation angle of the rotary filter 410 via the filter control unit 420, thereby switching a wavelength range of the illumination light IL supplied to the light guide 131 passing through the rotary filter 410.

Figure 5:
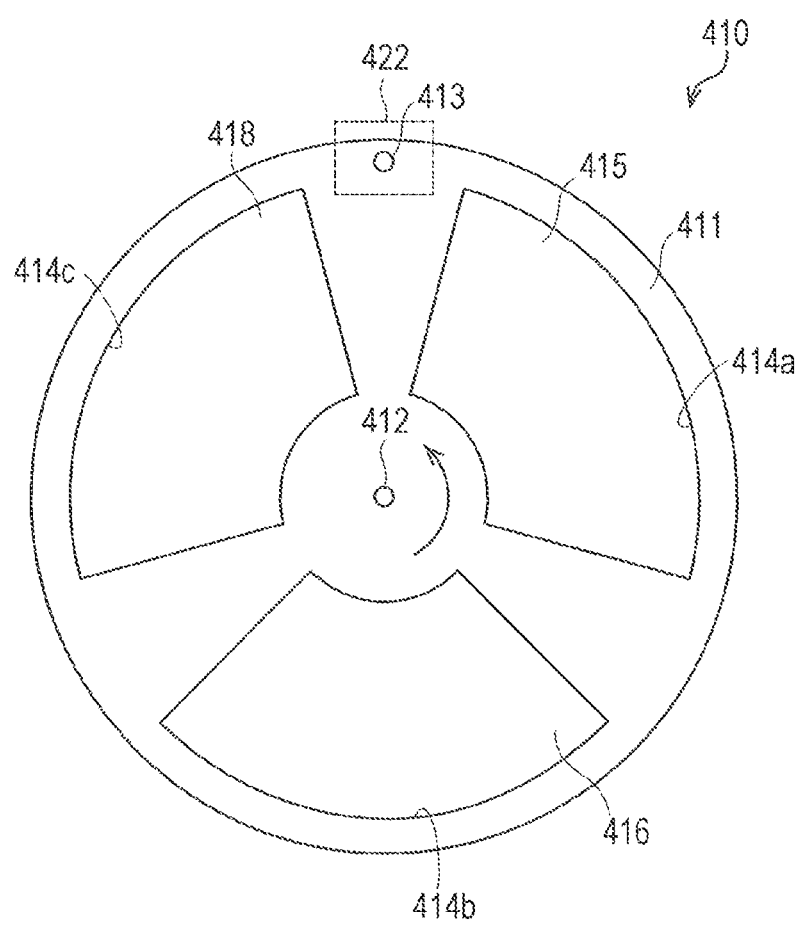
FIG. 5 is an external view (front view) of an example of a rotary filter used in a light source device of the endoscope system used in the present embodiment.

FIG. 5 is an external view (front view) of the rotary filter 410. The rotary filter 410 includes a substantially discoid frame 411 and three fan-shaped optical filters 415, 416, and 418. Three fan-shaped windows 414a, 414b, and 414c are formed at equal intervals around a central axis of the frame 411, and the optical filters 415, 416, and 418 are fitted to the windows 414a, 414b, and 414c, respectively. Incidentally, all the optical filters of the present embodiment are the dielectric multilayer film filters, but other types of optical filters (for example, an absorption-type optical filter, an etalon filter using a dielectric multilayer film as a reflective film) may be used.

In addition, a boss hole 412 is formed on the central axis of the frame 411. An output shaft of a servomotor (not illustrated) provided in the filter control unit 420 is inserted and fixed in the boss hole 412, and the rotary filter 410 rotates together with the output shaft of the servo motor.

When the rotary filter 410 rotates in a direction indicated by an arrow in FIG. 5, the optical filter on which light is incident switches in the order of the optical filters 415, 416, and 418 so that a wavelength band of the illumination light IL passing through the rotary filter 410 is sequentially switched.

Figure 6:
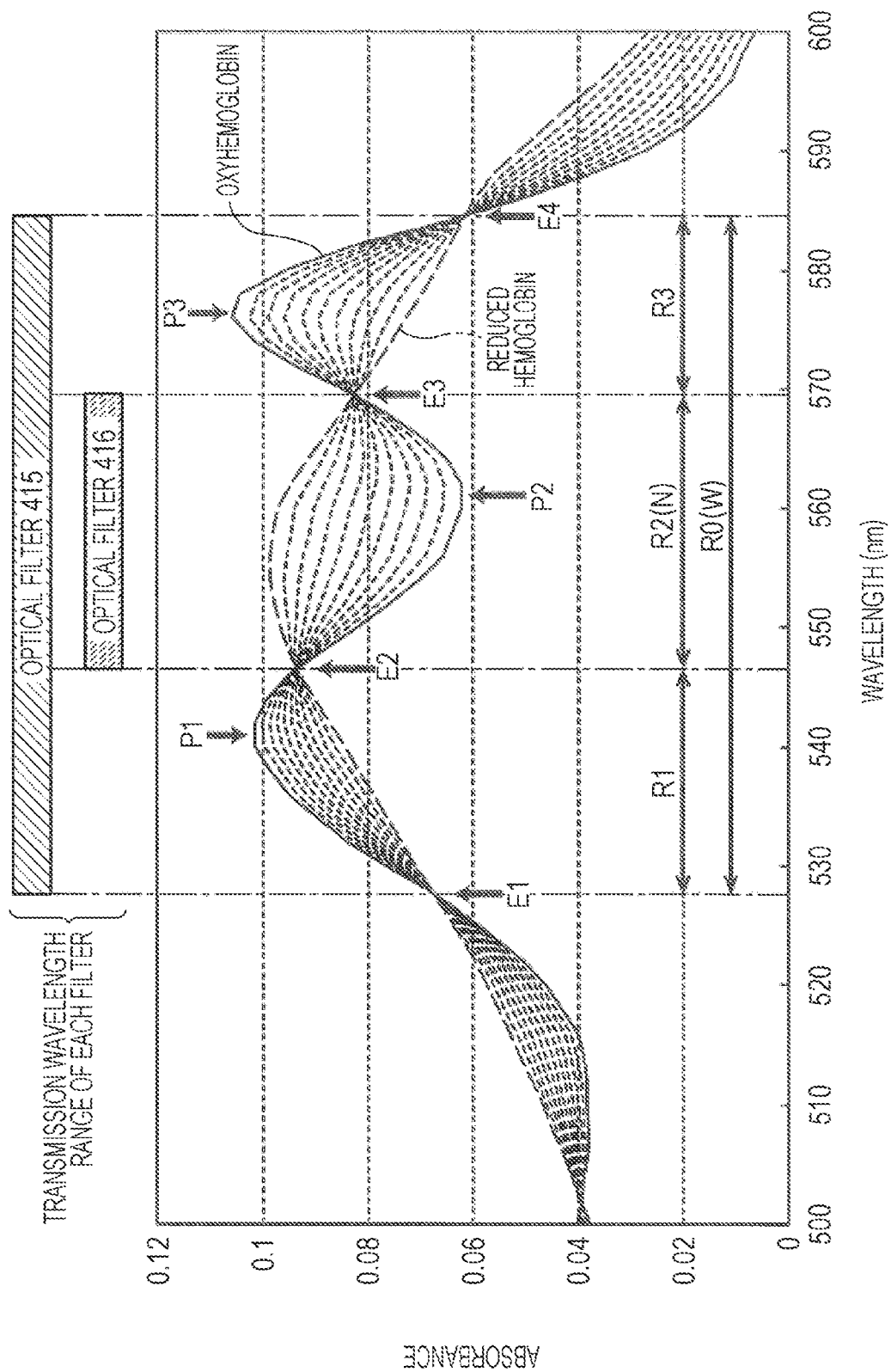
FIG. 6 is a graph illustrating an example of an absorption spectrum of hemoglobin in the vicinity of 550 nm.

The optical filters 415 and 416 are optical band pass filters that selectively pass light in a band of 550 nm. As illustrated in FIG. 6, the optical filter 415 is configured to pass light in a wavelength range R0 (W band) from isosbestic points E1 to E4 with a low loss and block light in other wavelength ranges. In addition, the optical filter 416 is configured to pass light in a wavelength range R2 (N band) from isosbestic points E2 to E3 with a low loss and to block light in the other wavelength ranges.

In addition, the optical filter 418 is an ultraviolet cut filter, and the light radiated from the light source lamp 430 transmits through the optical filter 418 in the visible light wavelength range. The light transmitted through the optical filter 418 is used as white light WL for imaging of a normal observation image. Incidentally, it may be configured such that the window 414c of the frame 411 is open without using the optical filter 418.

Therefore, the light transmitted through the optical filter 415 out of the light radiated from the light source lamp 430 is hereinafter referred to as Wide light, the light transmitted through the optical filter 416 out of the light radiated from the light source lamp 430 is hereinafter referred to as Narrow light, and the light transmitted through the optical filter 418 out of the light emitted from the light source lamp 430 is hereinafter referred to as the white light WL.

FIG. 6 is a graph illustrating an example of the absorption spectrum of hemoglobin in the vicinity of 550 nm.

As illustrated in FIG. 6, a wavelength range R1 is a band including a peak wavelength of an absorption peak P1 derived from oxyhemoglobin, a wavelength range R2 is a band including a peak wavelength of an absorption peak P2 derived from reduced hemoglobin, and a wavelength range R3 is a band including a peak wavelength of an absorption peak P3 derived from oxyhemoglobin. In addition, the wavelength range R0 includes the respective peak wavelengths of the three absorption peaks P1, P2, and P3.

In addition, the wavelength range R0 of the optical filter 415 and the wavelength range R2 of the optical filter 416 are included in the passing wavelength range (see FIG. 4) of the G color filter of the color filter 141a. Therefore, an image of the living tissue T formed by the light passing through the optical filter 415 or 416 is obtained as an image of the G component of the color image data imaged by the imaging element 141.

A through-hole 413 is formed in a peripheral edge portion of the frame 411. The through-hole 413 is formed at the same position (phase) as that of a boundary between the window 414a and the window 414c in a rotation direction of the frame 411. A photo-interrupter 422 configured to detect the through-hole 413 is arranged around the frame 411 so as to surround a part of the peripheral edge portion of the frame 411. The photo-interrupter 422 is connected to the filter control unit 420.

In this manner, the light source device 400 of the present embodiment is preferably configured so as to sequentially switch the plurality of optical filters 415, 416, and 418 in the optical path of the light radiated from the light source lamp 430 to emit the beams of light having different wavelength ranges, that is, the Wide light, the Narrow light, and the white light WL as the illumination light IL.

(Calculation of Feature Amount of Living Tissue)

The feature amount (the hemoglobin concentration or the hemoglobin oxygen saturation) of the living tissue T is calculated by the feature amount acquisition unit 510 of the processor 500. Hereinafter, a description will be given regarding a process of calculating the hemoglobin concentration and the hemoglobin oxygen saturation of the living tissue T from the image of the imaged living tissue T as the feature amounts.

As illustrated in FIG. 6, hemoglobin has a strong absorption band which is called Q band and derived from porphyrin in the vicinity of 550 nm. The absorption spectrum of hemoglobin changes according to an oxygen saturation that represents a proportion of oxyhemoglobin HbO in the total hemoglobin. A waveform of a solid line in FIG. 6 is an absorption spectrum where an oxygen saturation is 100%, that is, the oxyhemoglobin HbO, and a waveform of a long broken line is an absorption spectrum where an oxygen saturation is 0%, that is, reduced hemoglobin Hb. In addition, short broken lines indicate absorption spectrums of hemoglobin at intermediate oxygen saturations of 10, 20, 30, . . . , and 90%, that is, a mixture of the oxyhemoglobin HbO and the reduced hemoglobin Hb.

As illustrated in FIG. 6, the oxyhemoglobin HbO and the reduced hemoglobin Hb have peak wavelengths different from each other in the Q band. Specifically, the oxyhemoglobin HbO has the absorption peak P1 in the vicinity of a wavelength of 542 nm and the absorption peak P3 in the vicinity of a wavelength of 576 nm. On the other hand, the reduced hemoglobin Hb has the absorption peak P2 in the vicinity of 556 nm. FIG. 6 illustrates the absorption spectrum when the sum of the concentrations of the oxyhemoglobin HbO and the reduced hemoglobin Hb is constant, and thus, the isosbestic points E1, E2, E3, and E4 at which an absorbance becomes constant appear regardless of ratios of the oxyhemoglobin HbO and the reduced hemoglobin Hb, that is, the oxygen saturation. In the following description, a wavelength band sandwiched between the isosbestic points E1 and E2 is the wavelength band R1 described above with the optical filter 410, a wavelength band sandwiched between the isosbestic points E2 and E3 is the wavelength band R2, a wavelength band sandwiched between the isosbestic points E3 and E4 is the wavelength band R3, and a wavelength band sandwiched between the isosbestic points E1 and E4, that is, a combined band of the wavelength bands R1, R2, and R3 is the wavelength band R0. Therefore, a wavelength band of the Wide light, which is transmitted light that has been transmitted through the optical filter 415 out of the light radiated from the light source lamp 430, is the wavelength band R0, and a wavelength band of the Narrow light, which is transmitted light that has been transmitted through the optical filter 416 out of the light radiated from the light source lamp 430, is the wavelength band R2.

As illustrated in FIG. 6, the absorption of hemoglobin increases or decreases linearly relative to the oxygen saturation in the wavelength bands R1, R2, and R3. Specifically, total values AR1 and AR3 of the absorbances of hemoglobin in the wavelength bands R1 and R3 increase linearly relative to the concentration of oxyhemoglobin, that is, the oxygen saturation. In addition, a total value AR2 of absorbances of hemoglobin in the wavelength band R2 increases linearly relative to the concentration of reduced hemoglobin.

Here, the oxygen saturation is defined by the following Formula (1).

Formula (1):

$$Sat = \frac{[HbO]}{[Hb] + [HbO]} \qquad \text{[Formula 1]}$$

wherein,
Sat: Oxygen Saturation
[Hb]: Concentration of Reduced Hemoglobin
[HbO]: Concentration of Oxyhemoglobin
[Hb]+[HbO]: Hemoglobin concentration (tHb)

In addition, Formula (2) and Formula (3) expressing the concentrations of the oxyhemoglobin HbO and the reduced hemoglobin Hb are obtained from Formula (1).

Formula (2):

$$[HbO]=Sat \cdot ([Hb]+[HbO]) \qquad \text{[Formula 2]}$$

Formula (3):

$$[Hb]=(1-Sat) \cdot ([Hb]+[HbO]) \qquad \text{[Formula 3]}$$

Therefore, the total values AR1, AR2, and AR3 of the absorbances of hemoglobin become feature amounts that depend on both the oxygen saturation and the hemoglobin concentration.

Here, it has been found that a total value of absorbances in the wavelength band R0 does not depend on the oxygen saturation but is a value determined by the hemoglobin concentration. Therefore, the hemoglobin concentration can be quantified based on the total value of absorbances in the wavelength band R0. In addition, the oxygen saturation can be quantified based on the total value of absorbances in the wavelength band R1, the wavelength band R2, or the wavelength band R3 and the hemoglobin concentration quantified based on the total value of absorbances of the wavelength band R0.

The feature amount acquisition unit 510 of the present embodiment includes a first image processing unit 510*a*, a second image processing unit 510*b*, and a third image processing unit 510*c*.

The first image processing unit 510*a* performs calculation and acquisition of a hemoglobin concentration of the living tissue T based on a first ratio, which will be described later, sensitive to the hemoglobin concentration of the living tissue T, and calculation and acquisition of a hemoglobin oxygen saturation of the living tissue T based on the calculated hemoglobin concentration and a second ratio, which will be described later, sensitive to the hemoglobin oxygen saturation. The fact that the first ratio is sensitive to the hemoglobin concentration means that a value of the first ratio also changes when the hemoglobin concentration changes. In addition, the fact that the second ratio is sensitive to the hemoglobin oxygen saturation means that a value of the second ratio also changes when the oxygen saturation changes.

As illustrated in FIG. 2(*b*), the second image processing unit 510*b* generates the mask image M as illustrated in FIG. 2(*c*) to mask the oxygen saturation distribution image from the hemoglobin concentration distribution image by setting, in the hemoglobin concentration distribution image, a pixel having a hemoglobin concentration less than a threshold as a non-transmissive pixel having a transmittance of zero and setting a pixel having the hemoglobin concentration equal to or more than the threshold as a transmissive pixel while giving the pixel a transmittance, determined in accordance with a degree of the deviation from the threshold, in the hemoglobin concentration distribution image. Specifically, the second image processing unit 510b generates the mask image M as illustrated in FIG. 2(c) to mask the oxygen saturation distribution image front the hemoglobin concentration distribution image by setting a pixel whose pixel value representing the hemoglobin concentration is equal to or more than a set lower limit value and is less than an upper limit value as the transmissive pixel while giving the pixel the transmittance determined in accordance with a ratio of a difference (distance) between the pixel value (pixel output value) and the lower limit value relative to a difference between the lower limit value and the upper limit value. According to one embodiment, it is preferable to set the pixel whose pixel value is equal to or more than the upper limit value as the transmissive pixel while giving the transmittance of 100% to the pixel.

The third image processing unit 510c generates the oxygen saturation distribution processed image in which the mask image M is superimposed on the upper layer of the oxygen saturation distribution image.

First, the generation of the hemoglobin concentration distribution image and the generation of the oxygen saturation distribution image, which are performed in the first image processing unit 510a, will be described.

(Generation of Hemoglobin Concentration Distribution Image and Oxygen. Saturation Distribution Image)

A value of an luminance component of the color image data of the living tissue T illuminated with the above-described Wide light (light in the wavelength band R0 transmitted through the optical filter 415) corresponds to the total value of absorbances in the wavelength band R0 described above, and thus, the first image processing unit 510a of the feature amount acquisition unit 510 of the present embodiment calculates the hemoglobin concentration based on the luminance component of the color image data in the wavelength band R0. Here, the luminance component is obtained by multiplying a value of the R component of the color image data by a predetermined coefficient, multiplying a value of the G component of the color image data by a predetermined coefficient, multiplying a value of the B component of the color image data by a predetermined coefficient, and summing up these multiplication results.

Specifically, the first image processing unit 510a of the feature amount acquisition unit 510 calculates the hemoglobin concentration based on a ratio Wide/WL(R), obtained by dividing a luminance component Wide (hereinafter, also simply referred to as Wide) of color image data (second color image data) of the living tissue T obtained using the Wide light (second light) as the illumination light IL by an R component WL(R) of color image data (first color image data) of the living tissue T obtained using the white light WL (first light) as the illumination light IL or a total component WL(R)+WL(G) of the R component WL(R) and a G component WL(G), or based on Wide/{WL(R)+WL(G)} (the first ratio). In the calculation of the hemoglobin concentration, the ratio Wide/WL(R) or Wide/{WL(R)+WL(G)} obtained by dividing the luminance component Wide by WL(R) or {WL(R) WL(G)} is used to remove a change in spectral characteristics of the living tissue T depending on the degree of scattering of the illumination light IL on the surface of the living tissue T. In particular, a reflection spectrum of the living tissue T, such as an inner wall of a digestive tract, is easily affected by wavelength characteristics of scattering of illumination light by the living tissue T in addition to wavelength characteristics of absorption by components constituting the living tissue T (specifically, absorption spectrum characteristics of oxyhemoglobin and reduced hemoglobin). The R component WL(R) of the color image data (first color image data) of the living tissue T obtained using the white light WL (first light) as the illumination light IL or the total component WL(R)+WL(G) of the R component and the G component indicates the degree of scattering of the illumination light IL in the living tissue T without being affected by the hemoglobin concentration and hemoglobin oxygen saturation. Therefore, in order to remove the influence of scattering in the living tissue T of the illumination light IL from the reflection spectrum of the living tissue T, a wavelength band of the white light WL (reference light) is preferably set to include a wavelength band in which one of components of the first color image data is insensitive to a change in hemoglobin concentration of the living tissue T. The fact that one of the components of the first color image data is insensitive to the change in hemoglobin concentration means that a value of the one of the components of the first color image data does not substantially change even if the hemoglobin concentration changes. Further, the wavelength band of the white light WL (reference light) is preferably set to include a wavelength band in Which one of the components of the first color image data is insensitive to a change in oxygen saturation. The fact that one of the components of the first color image data is insensitive to the change in oxygen saturation means that a value of the one of the components of the first color image data does not substantially change even if the oxygen saturation changes.

In the present embodiment, a reference table, which indicates a correspondence relationship between information of the first ratio and the hemoglobin concentration in the sample reproducing the absorption characteristic of hemoglobin with the predetermined concentration, is stored in advance in the memory 512, and the first image processing unit 510a of the feature amount acquisition unit 510 uses this reference table to calculate a hemoglobin concentration based on a value of the first ratio in the captured color image data of the living tissue T.

Although it is preferable to use the ratio Wide/WL(R) between the luminance component Wide of the color image data (second color image data) of the living tissue T obtained using the Wide light (second light) as the illumination light IL and the R component WL(R) of the color image data (first color image data) of the living tissue T obtained using the white light WL (first light) as the illumination light IL or the total component WL(R)+WL(G) of the R component WL(R) and the G component WL(G), or Wide/{WL(R)+WL(G)}, as the first ratio in the calculation of the hemoglobin concentration in the present embodiment, it is also preferable to use a G component Wide(G) instead of the luminance component Wide of the color image data (second color image data) of the living tissue T obtained using the Wide light (second light) as the illumination light IL.

Further, the total value of absorbances in the wavelength band R2 decreases along with the increase of the oxygen saturation, and the total value of absorbances in the wavelength band R0 changes depending on the hemoglobin concentration but is constant regardless of the change of the oxygen saturation as described above. Thus, the oxygen saturation calculation unit 510b of the feature amount acquisition unit 510 calculates the oxygen saturation based on a second ratio to be defined below. That is, the oxygen saturation calculation unit 510b of the feature amount acquisition unit 510 calculates a ratio Narrow/Wide, as the second ratio, between a luminance component Narrow (hereinafter, also simply referred to as Narrow) of color image data (third color image data) of the living tissue T illuminated with the Narrow light, which is the light of the wavelength band R2 that has passed through the optical filter 416, and the luminance component Wide of the color image data (second color image data) of the living tissue T illuminated with the Wide light (light of the wavelength band R0 transmitted through the optical filter 415). On the other hand, a correspondence relationship indicating a relationship between the hemoglobin concentration and a lower limit value of the second ratio at the oxygen saturation=0% and an upper limit value of the second ratio Narrow/Wide at the oxygen saturation=100% is obtained from the sample, and stored in memory 512 in advance. The oxygen saturation calculation unit 510b of the feature amount acquisition unit 510 uses a calculation result of the hemoglobin concentration obtained from the color image data generated by imaging the living tissue T and the above correspondence relationship to obtain the lower limit value and the upper limit value of the second ratio. The lower limit value and the upper limit value are values corresponding to the oxygen saturations 0% and 100%, respectively. Further, the oxygen saturation calculation unit 510b calculates the oxygen saturation based on any position in a range between the lower limit value and the upper limit value corresponding to the oxygen saturation 0 to 100% where the value of the second ratio Narrow/Wide of the imaged living tissue T is present by utilizing the fact that the second ratio changes linearly depending on the oxygen saturation between the obtained lower limit value and upper limit value. In this manner, the oxygen saturation calculation unit 510b of the feature amount acquisition unit 510 calculates the oxygen saturation.

In addition, a reference table, which indicates a correspondence relationship between the hemoglobin concentration and the value of the second ratio, and the hemoglobin oxygen saturation, is obtained from the sample and stored in the memory 512 in advance, and the hemoglobin oxygen saturation can also be calculated from the calculated second ratio with reference to this reference table.

In the present embodiment, the second ratio is used as the ratio between the luminance component Narrow of the color image data (third color image data) of the living tissue T illuminated with the Narrow light and the luminance component Wide of the color image data (second color image data) of the living tissue T illuminated with the Wide light. However, it is also possible to use a ratio between a G component Narrow(G) of the color image data (third color image data) of the living tissue T illuminated with the Narrow light and the G component Wide(G) of the color image data (second color image data) of the living tissue T illuminated with the Wide light, and it is desirable to optimize the ratio in accordance with a wavelength characteristic of a filter to be used.

In addition, the Narrow light in the wavelength band R2 is used to illuminate the living tissue T in order for the calculation of the second ratio in the present embodiment, but the light to be used is not limited to the Narrow light. For example, it is also possible to use light whose wavelength band is the wavelength band R1 or the wavelength band R2 with an intention of use of the wavelength band R1 or the wavelength band R2 where the total value of absorbances changes with the change of the oxygen saturation. In this case, a filter characteristic of the optical filter 416 may be set to the wavelength band R1 or the wavelength band R2.

As described above, the ratio Wide/WL(R) or Wide/{WL(R) WL(G)} is a ratio that is sensitive to the hemoglobin concentration of the living tissue, the ratio Narrow/Wide is a ratio sensitive to the hemoglobin oxygen saturation of the living tissue, the luminance component Wide is the component of the wavelength band in the range of 500 nm to 600 nm, and Narrow is the component of the wavelength band narrower than the above-described wavelength band in the range of 500 nm to 600 nm in the present embodiment. As a result, the hemoglobin concentration and the hemoglobin oxygen saturation can be accurately obtained while minimizing the influence of disturbance such as scattering.

Figure 7:
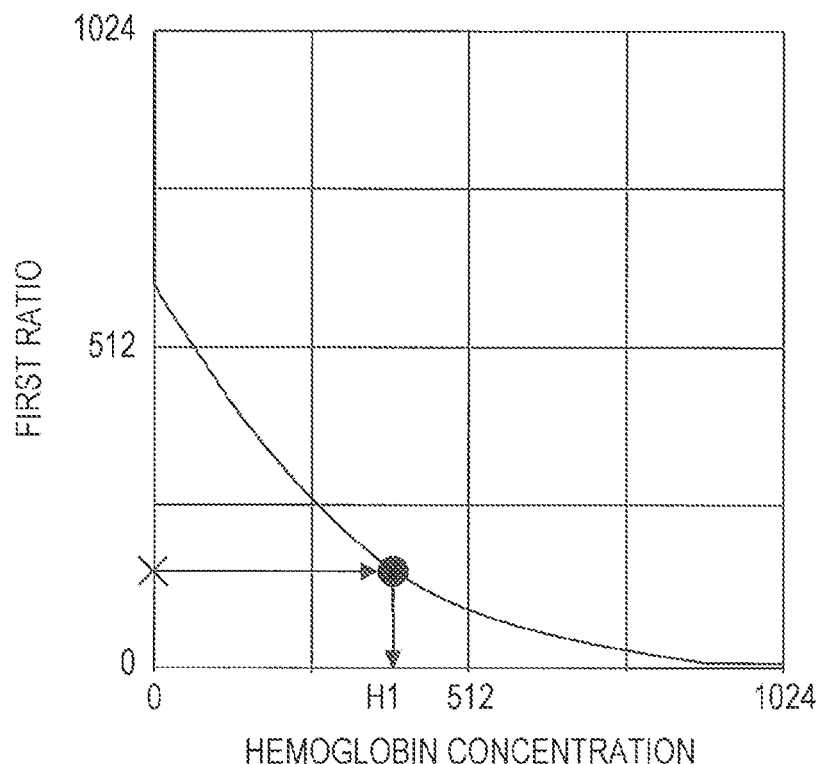
FIG. 7 is a graph illustrating an example of a relationship between a first ratio used in the present embodiment and a hemoglobin concentration.

FIG. 7 is a graph illustrating an example of a relationship between the first ratio and the hemoglobin concentration. When obtaining the first ratio as described above, the first image processing unit 510a of the feature amount acquisition unit 510 refers to a reference table indicating the correspondence relationship as illustrated in FIG. 7 to obtain the hemoglobin concentration based on the determined first ratio. FIG. 7 indicates that a concentration H1 of hemoglobin has been obtained based on a value of the first ratio. The numerical values on the horizontal and vertical axes in FIG. 7 are indicated by values of 0 to 1024 for convenience.

Figure 8:
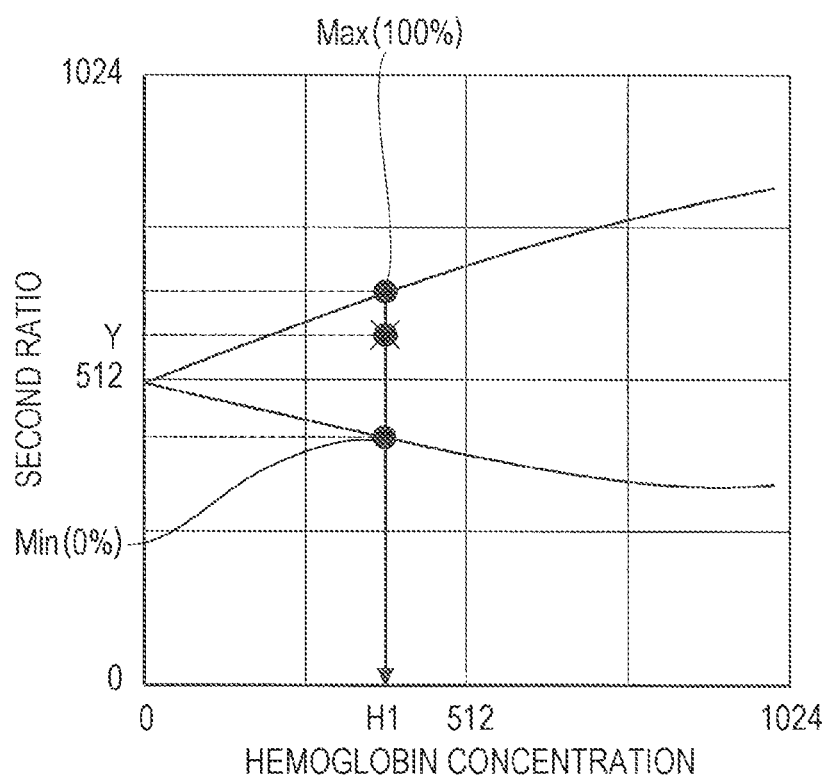
FIG. 8 is a graph illustrating an example of a relationship between an upper limit value and a lower limit value of a second ratio used in the present embodiment, and the hemoglobin concentration.

FIG. 8 is a graph illustrating an example of a relationship between the upper limit value and the lower limit value of the second ratio, and the hemoglobin concentration. The numerical values on the horizontal and vertical axes in FIG. 8 are indicated by values of 0 to 1024 for convenience.

When obtaining the second ratio as described above, the first image processing unit 510a of the feature amount acquisition unit 510 obtains the upper limit value and the lower limit value of the second ratio in the obtained hemoglobin concentration using the correspondence relationship illustrated in FIG. 8 based on the hemoglobin concentration and the second ratio obtained by the first image processing unit 510a. The upper limit value indicates the oxygen saturation=100%, and the lower limit value indicates the oxygen saturation=0%. The oxygen saturation calculation unit 510b obtains a value of the oxygen saturation by obtaining any position between the upper limit value and the lower limit value where the second ratio is present. In FIG. 8, an upper limit value Max (100%) and a lower limit value Min (0%) at the concentration H1 of hemoglobin when a value of the second ratio is R2 are obtained. The value of the oxygen saturation is obtained based on the upper limit value Max (100%), the lower limit value Min (0%), and a value Y of the second ratio.

The first image processing unit 510a uses pixel values obtained by performing gradation processing based on a value of the hemoglobin concentration and a value of the oxygen saturation calculated in this manner for each pixel to generate the hemoglobin concentration distribution image and the oxygen saturation distribution image.

(Generation of Mask Image and Generation of Oxygen Saturation Distribution Processed Image)

As illustrated in FIG. 2(b), in the generation of the mask image performed by the second image processing unit 510, the mask image M as illustrated in FIG. 2(c) to mask the oxygen saturation distribution image is generated from the hemoglobin concentration distribution image by, in the hemoglobin concentration distribution image, setting the pixel having the hemoglobin concentration less than the threshold as the non-transmissive pixel having the transmittance of zero and setting the pixel having the hemoglobin concentration equal to or more than the threshold as the transmissive pixel while giving the pixel the transmittance, determined in accordance with the degree of the hemoglobin concentration deviating from the threshold.

Specifically, the pixel whose pixel value (pixel output value) representing the hemoglobin concentration is less than the set lower limit is set as the non-transmissive pixel having the transmittance of zero, the pixel whose pixel value is equal to or more than the set upper limit is set as the transmissive pixel having the transmittance of 100%, and the pixel whose pixel value (pixel output value) is between the lower limit value and the upper limit value is set as the transmissive pixel while giving the pixel an intermediate transmittance between 0 and 100% to be modulated in accordance with the ratio of the difference between the pixel value and the lower limit relative to the difference between the lower limit and the upper limit, thereby generating the mask image M (see FIG. 2(c)) as illustrated in FIG. 2(c) to mask the oxygen saturation distribution image from the hemoglobin concentration distribution image. Here, the threshold, the upper limit value, and the lower limit value may be values set in advance, or may be values that can be freely input and set by an operator.

The third image processing unit 510c generates the oxygen saturation distribution processed image in which the generated mask image M is superimposed on the upper layer of the oxygen saturation distribution image generated by the first image processing unit 510a. Data of the generated oxygen saturation distribution processed image is controlled to a display form of a predetermined image through the image display control unit 514 and is output to the display 300.

Figure 9:
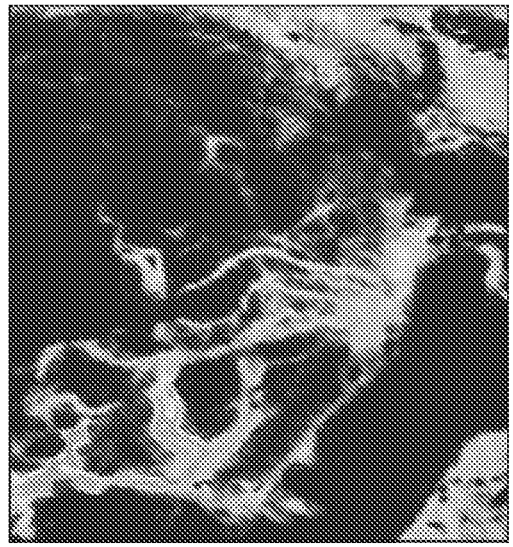
FIG. 9(a) is a view illustrating an example of a diagnosis support image displayed by the endoscope system of the present embodiment.
FIG. 9(b) is an example of a diagnosis support image displayed by a conventional endoscope system.
Figure 9:
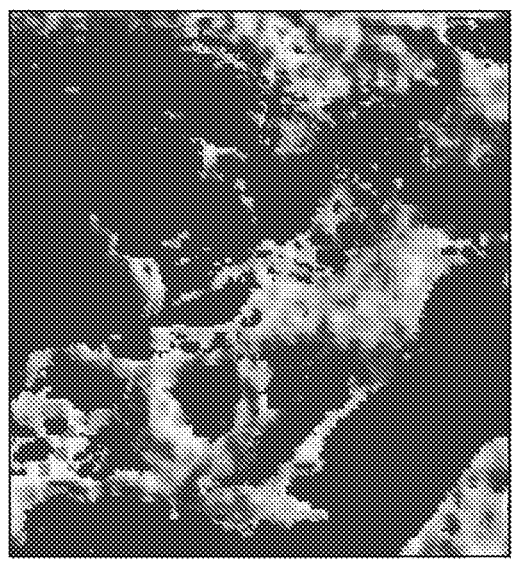

FIG. 9(a) is a view illustrating an example of a diagnosis support image of the present embodiment displayed by the endoscope system 10, and FIG. 9(b) is an example of a diagnosis support image displayed by a conventional endoscope system. Specifically, FIGS. 9(a) and 9(b) are the views illustrating the examples of the oxygen saturation distribution processed image (diagnosis support image) of the present embodiment, which is generated from the distribution image of the same hemoglobin concentration and the distribution image of the oxygen saturation, and a conventional oxygen saturation distribution image, and illustrate a part surrounded by a rectangular frame F in FIGS. 1(a) and 1(c).

As illustrated in FIG. 9(a), it can be understood that image information in a muscle-like form such as a blood vessel is displayed in the diagnosis support image (oxygen saturation distribution processed image) generated in the present embodiment. On the other hand, the conventional diagnosis support image illustrated in FIG. 9(b) is an image which is merely displayed by selecting a pixel with a designated hemoglobin concentration.

That is, in this oxygen saturation distribution image, image information in the muscle-like form such as the blood vessel is not displayed. Thus, it is difficult to indicate which part on the living tissue illustrated in FIG. 1(a) is the non-healthy part that becomes a problem in the conventional diagnosis support image. In the diagnosis support image generated in the present embodiment, however, the mask is generated based on the change in hemoglobin concentration (blood), and thus, the image information in the muscle-like form such as the blood vessel is displayed so that it is possible to easily identify which part on the living tissue illustrated in FIG. 1(a) is the non-healthy part that becomes a problem based on the image information.

FIGS. 10(a) to 10(f) are views for describing the mask image M used to create the diagnosis support image to be displayed by the endoscope system 10. Specifically, FIGS. 10(a) to 10(f) illustrate examples of gradation conversion when generating values of 0 to 100% of the transmittance from a value of the hemoglobin concentration for creation of the mask image M.

Figure 10A:
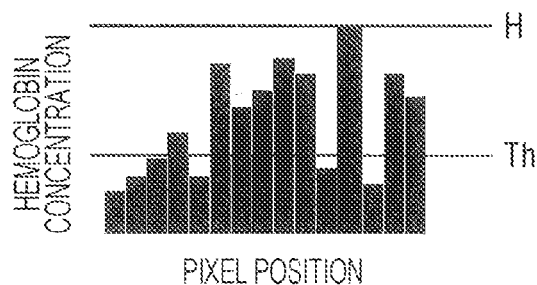
FIGS. 10(a) to 10(f) are views for describing a mask image used to create a diagnosis support image to be displayed by the endoscope system or the image display device of the present embodiment.
Figure 10B:
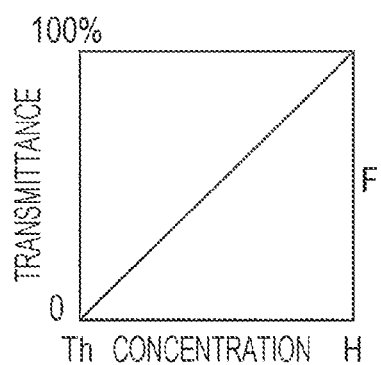
Figure 10C:
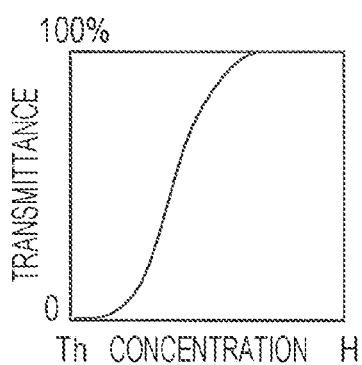
Figure 10D:
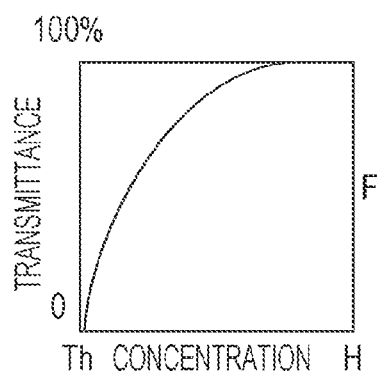
Figure 10E:
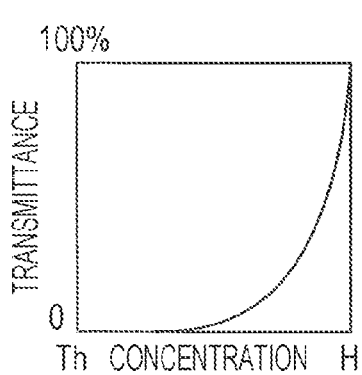
Figure 10F:
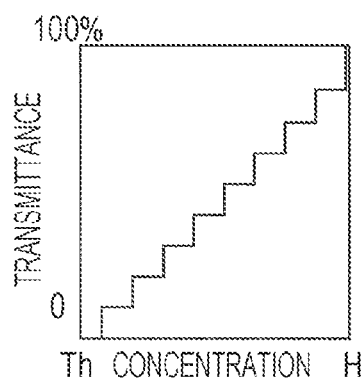

As illustrated in FIG. 10(a), when a threshold Th of the hemoglobin concentration and an upper limit value H are defined, the conversion from the hemoglobin concentration to the transmittance between the threshold Th and the upper limit value H can be performed using the gradation conversion as illustrated in FIGS. 10(b) to 10(f). A pixel whose hemoglobin concentration is less than the threshold Th is set as the non-transmissive pixel having the transmittance of zero. According to one embodiment, the transmittance can be changed linearly with respect to the concentration between the threshold Th and the upper limit value H as in the gradation conversion illustrated in FIG. 10(b). According to one embodiment, non-linear conversion can be also performed between the threshold Th and the upper limit value H such that the change of the transmittance with respect to the concentration decreases near the threshold Th and the upper limit value H and the change of the transmittance with respect to the concentration increases in an intermediate region between the threshold Th and the upper limit value H as in the gradation conversion illustrated in FIG. 10(c). According to one embodiment, non-linear conversion can be also performed such that the change of the transmittance with respect to the concentration gradually decreases along with the increase in concentration between the threshold Th and the upper limit value H as in the gradation conversion illustrated in FIG. 10(d). According to one embodiment, non-linear conversion can be also performed such that the change of the transmittance with respect to the concentration gradually increases along with the increase in concentration between the threshold Th and the upper limit value H as in the gradation conversion illustrated in FIG. 10(e). According to one embodiment, instead of the conversion illustrated in FIG. 10(b) in which the transmittance changes linearly and continuously with respect to the change of the concentration, conversion can be also performed such that the transmittance changes stepwise as the concentration increases as in the gradation conversion illustrated in FIG. 10(f). According to one embodiment, the conversion can be also performed such that the transmittance changes stepwise as illustrated in FIG. 10(f), instead of the conversion in which the transmittance changes continuously with respect to the change of the concentration as illustrated in FIGS. 10(c) to 10(e).

In this manner, the transmittance of the transmissive pixel of the mask image M is set so as to increase continuously or stepwise as the pixel value of the pixel deviates more from the threshold Th in the embodiment. As a result, it is easy to display the image information in the muscle-like form such as the blood vessel, and thus, it is easy to identify which part on the living tissue illustrated in FIG. 1(a) is the non-healthy part that becomes a problem.

In this case, it is preferable that the transmittance of the transmissive pixel increase nonlinearly as the pixel value of the pixel deviates more from the threshold Th.

Incidentally, it is preferable that the processor 200 include an input unit (not illustrated) that receives an input that continuously changes a value of the threshold Th, and that the third image processing unit 510c generate the oxygen saturation distribution processed image each time the input is changed. As a result, an operator can adjust the threshold Th so as to display the image information with which it is possible to identify the part on the living tissue in the muscle-like form such as the blood vessel while viewing the oxygen saturation distribution processed image displayed on the display 300, and thus, the operator can easily indicate the location of the non-healthy part on the living tissue.

The endoscope system 10 of the present embodiment can provide the diagnosis support image with which it is possible to easily indicate the non-healthy part on the image of the living tissue by imaging the living tissue and performing the image processing using the mask image M. Instead of the endoscope system 10, however, it is also possible to provide an image display device configured to receive an imaged image of a living tissue or an image display device in which the imaged image of the living tissue has been stored in advance in a memory.

That is, the image display device includes a processor that performs image processing and a display configured to display an image.

The processor includes first to third image processing units to generate an oxygen saturation distribution processed image. The display is configured to display the oxygen saturation distribution processed image generated by the processor.

Here, the first image processing unit is configured to obtain the hemoglobin concentration distribution image of the living tissue and the oxygen saturation distribution image of the living tissue from the imaged image of the living tissue. The second image processing unit generates the mask image M to mask the oxygen saturation distribution image from the hemoglobin concentration distribution image by setting, in the hemoglobin concentration distribution image, a pixel having a hemoglobin concentration less than the threshold Th as a non-transmissive pixel having a transmittance of zero and setting a pixel having the hemoglobin concentration equal to or more than the threshold Th as a transmissive pixel while giving the pixel a transmittance, determined in accordance with a degree of a pixel value of the pixel deviating from the threshold Th. The third image processing unit is configured to generate the oxygen saturation distribution processed image in which the mask image M is superimposed on an upper layer of the oxygen saturation distribution image.

Even in this image display device, the oxygen saturation distribution processed image based on the mask image M is generated, and thus, the diagnosis support image that enables determination on presence of the non-healthy part can be displayed including the image information with which it is possible to identify the position of the non-healthy part in the living tissue.

Although the wavelength band of the illumination light IL used to calculate the hemoglobin concentration and hemoglobin oxygen saturation is in the range of 500 to 600 nm as illustrated in FIG. 6 in the above embodiment, the disclosure is not limited to this wavelength band. For example, the disclosure can be also applied to a wavelength band in which an absorbance changes around an isosbestic point depending on the hemoglobin oxygen saturation. For example, a constant wavelength band on the long wavelength side or the short wavelength side of any isosbestic point in a wavelength band of 400 to 500 nm can be also used as the wavelength band of illumination light IL.

Although the present embodiment has been described as above, the present disclosure is not limited to the above embodiment, and various modifications can be made within a scope of a technical idea of the present disclosure.

REFERENCE SIGNS LIST 10 endoscope system
100 electronic endoscope
110 insertion tube
111 insertion tube distal end
121 objective lens group
131 light guide
131a distal end
131b proximal end
132 lens
141 imaging element
141a color filter
142 cable
200 processor
300 display
400 light source device
410 rotary filter
420 filter control unit
430 light source lamp
440 condenser lens
450 condenser lens
500 image processing unit
502 A/D conversion circuit
504 image pre-processing unit
506 frame memory unit
508 image post-processing unit
510 feature amount acquisition unit
510a first image processing unit
510b second image processing unit
510c third image processing unit
512 memory
514 image display control unit
516 controller

The invention claimed is:

1. An endoscope system comprising:
an endoscope including an image sensor configured to generate a plurality of pieces of image data by imaging a living tissue;
a processor including:
a first image processor configured to obtain a hemoglobin concentration distribution image representing a distribution of a hemoglobin concentration of the living tissue and a hemoglobin oxygen saturation distribution image representing a distribution of a hemoglobin oxygen saturation of the living tissue from the plurality of pieces of image data;
a second image processor configured to generate a mask image to mask the hemoglobin oxygen saturation distribution image from the hemoglobin concentration distribution image by, in the hemoglobin concentration distribution image, setting a first pixel having the hemoglobin concentration less than a predetermined threshold as a non-transmissive pixel having a transmittance of zero and setting a second pixel having the hemoglobin concentration equal to or more than the predetermined threshold as a transmissive pixel while giving the second pixel a transmittance, corresponding to one level of a plurality transmittance levels, determined in accordance with a degree of the hemoglobin concentration deviating from the threshold; and
a third image processor configured to generate a hemoglobin oxygen saturation distribution processed image by superimposing the mask image on an upper layer of the hemoglobin oxygen saturation distribution image to change a luminance value thereof; and
a display configured to display the hemoglobin oxygen saturation distribution processed image generated by the third image processor.

2. The endoscope system according to claim 1, wherein the transmittance of the transmissive pixel increases continuously or stepwise as the hemoglobin concentration of the second pixel deviates more from the threshold.

3. The endoscope system according to claim 2, wherein the transmittance of the transmissive pixel increases nonlinearly as the hemoglobin concentration of the second pixel deviates more from the threshold.

4. The endoscope system according to claim 1, wherein the processor includes an input unit configured to receive an input that continuously changes a value of the threshold, and the third image is configured to generate the hemoglobin oxygen saturation distribution processed image each time the input is changed.

5. The endoscope system according to claim 1, wherein the first image processor calculates values of a first ratio and a second ratio between predetermined components using values of the components out of components of the plurality of pieces of image data, and calculates the hemoglobin concentration and the hemoglobin oxygen saturation using the values of the first ratio and the second ratio.

6. The endoscope system according to claim 5, wherein the first ratio is a ratio sensitive to the hemoglobin concentration of the living tissue,
the second ratio is a ratio sensitive to the hemoglobin oxygen saturation of the living tissue,
one of the components of the image data used for calculation of the first ratio is a component of a first wavelength band within a range of 500 nm to 600 nm, and
one of the components of the image data used for calculation of the second ratio is a component of a second wavelength band narrower than the first wavelength band.

7. An image display device comprising:
a processor configured to perform image processing; and
a display configured to display an image,
wherein the processor includes:
a first image processor configured to obtain a hemoglobin concentration distribution image representing a distribution of a hemoglobin concentration of a living tissue and a hemoglobin oxygen saturation distribution image representing a distribution of a hemoglobin oxygen saturation of the living tissue from an imaged image of the living tissue;
a second image processor configured to generate a mask image to mask the hemoglobin oxygen saturation distribution image from the hemoglobin concentration distribution image by, in the hemoglobin concentration distribution image, setting a first pixel having the hemoglobin concentration less than a predetermined threshold as a non-transmissive pixel having a transmittance of zero and setting a second pixel having the hemoglobin concentration equal to or more than the predetermined threshold as a transmissive pixel while giving the second pixel a transmittance, corresponding to one level of a plurality transmittance levels, determined in accordance with a degree of hemoglobin concentration deviating from the threshold; and
a third image processor configured to generate a hemoglobin oxygen saturation distribution processed image by superimposing the mask image on an upper layer of the hemoglobin oxygen saturation distribution image to change a luminance value thereof, and
the display is configured to display the hemoglobin oxygen saturation distribution processed image generated by the third image processor.

* * * * *